United States Patent [19]
Gonser

[11] Patent Number: 4,966,552
[45] Date of Patent: Oct. 30, 1990

[54] STERILIZABLE NON-LUBRICATED ROTARY INSTRUMENT FOR DENTAL AND MEDICAL USE

[75] Inventor: Donald I. Gonser, Lancaster, Pa.
[73] Assignee: Den-Tal-Ez, Inc., Audubon, Pa.
[21] Appl. No.: 348,722
[22] Filed: May 8, 1989
[51] Int. Cl.$^5$ ............................................. A61C 1/05
[52] U.S. Cl. ................................. 433/132; 415/229; 415/904; 384/492
[58] Field of Search ............. 433/132; 415/904, 170.1, 415/229; 384/492

[56] References Cited

U.S. PATENT DOCUMENTS

| | | | |
|---|---|---|---|
| 1,332,176 | 2/1920 | Heindlhofer | 384/492 |
| 2,158,156 | 5/1939 | Schroder | 384/492 |
| 2,534,929 | 12/1950 | Schultz et al. | 384/492 |
| 3,071,861 | 1/1963 | Saffir | 433/132 |
| 3,097,897 | 7/1963 | Taylor | 384/492 |
| 3,248,792 | 5/1966 | Staunt | 433/132 |
| 3,421,224 | 1/1969 | Brehm et al. | 433/132 |
| 3,469,318 | 9/1969 | Saffir | 433/132 |
| 3,491,423 | 1/1970 | Haller | 384/492 |
| 4,153,993 | 5/1979 | Kataoka et al. | 433/132 |
| 4,249,896 | 2/1981 | Kerfoot, Jr. | 433/132 |
| 4,568,642 | 2/1986 | DeForrest et al. | 433/132 |
| 4,770,549 | 9/1988 | Rokkaku et al. | 384/492 |
| 4,792,244 | 12/1988 | Yamashita et al. | 384/492 |

OTHER PUBLICATIONS

"Evaluation of Roller Bearings Containing Hot Pressed Silicon Nitride Rolling Elements" by H. R. Baumgartner, Paper presented at 2nd Army Materials Technology Conference, Ceramics for High Performance Applications, Hyannis, MA, Nov. 13–16, 1973.
"Hydraulic Turbine Contra–Angle Landpiece", Nelson et al., Journal of the Amer. Dent. Assoc., vol. 47, pp. 324–329, 1953.

Primary Examiner—John J. Wilson
Attorney, Agent, or Firm—Howson and Howson

[57] ABSTRACT

A handpiece particularly suited for medical/dental applications in which a rotary tool is used upon and in proximity with anatomical structures. The handpiece has an anti-friction bearing assembly which mounts the rotary tool. At least the rolling elements of the bearing assembly are formed of ceramic material. The instrument may be sterilized repeatedly without requiring lubrication either in use or between sterilization cycles.

20 Claims, 2 Drawing Sheets

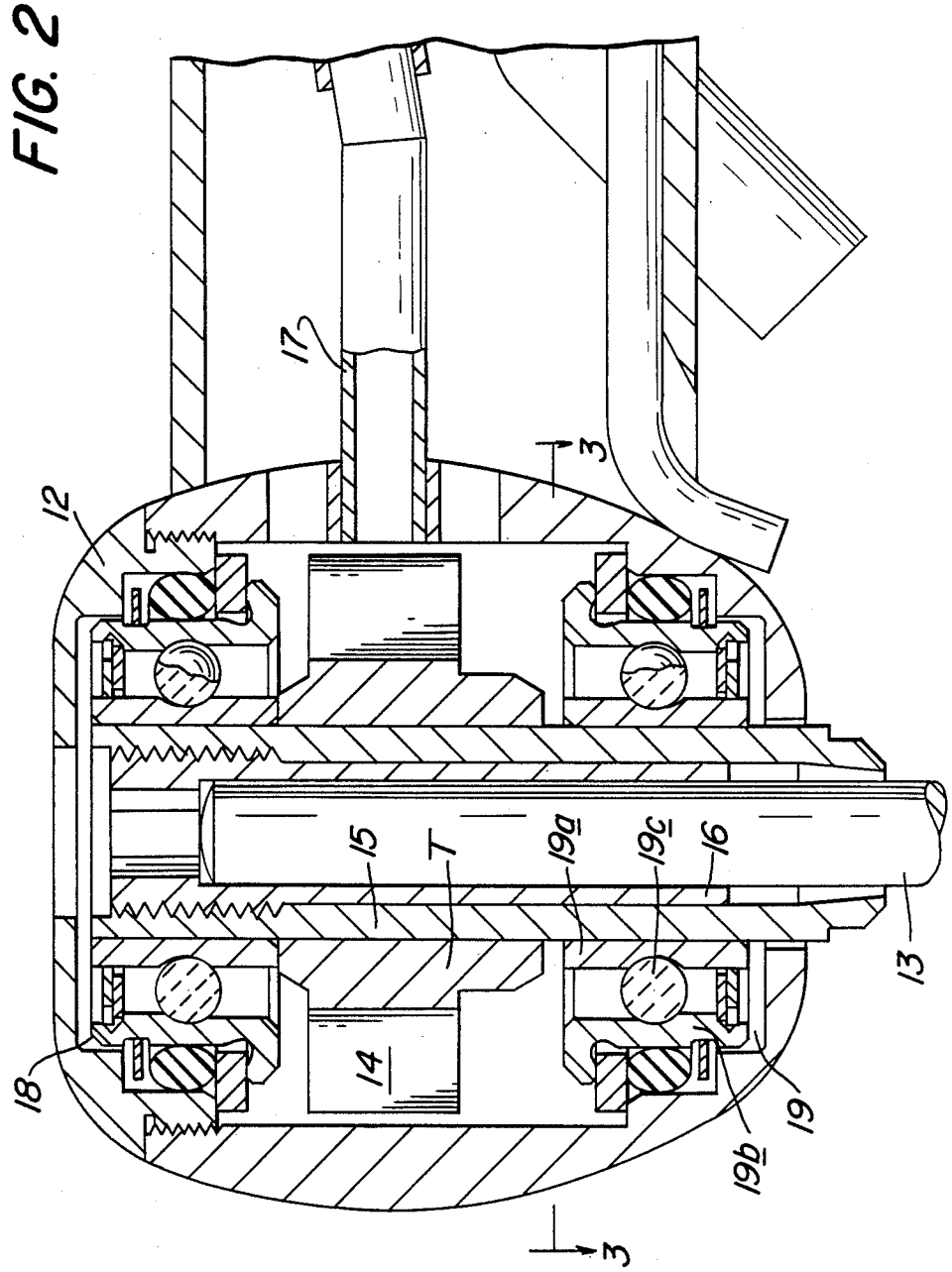

STERILIZABLE NON-LUBRICATED ROTARY INSTRUMENT FOR DENTAL AND MEDICAL USE

FIELD OF THE INVENTION

The present invention relates to dental/medical mechanically power driven instruments, and more particularly, the present invention relates to a non-lubricated dental handpiece having an anti-friction bearing assembly wherein at least the rolling elements are formed of ceramic material.

BACKGROUND OF THE INVENTION

In recent years, there is an increasing interest in the heat sterilization of powered instruments for use in medical and dental applications to limit the transmission of communicable diseases. Such powered instruments, over the course of their useful lives, may be subjected to many cycles of sterilization. Commercially desirable powered instruments, or handpieces, must be capable of withstanding repeated sterilization cycles without adversely affecting their operability.

Certain powered instruments, such as a dental handpiece, may have a high speed turbine rotatably supported in the proximal end of the handpiece by a pair of anti-friction bearing assemblies to accommodate radial and thrust loads applied in some dentistry procedures. These bearings are quite small, having rolling elements, or balls, about one millimeter in diameter. The raceways and balls are usually fabricated of stainless steel.

In many high speed dental handpieces, air-driven turbines rotate tools, such as drills and burrs, at velocities exceeding 400,000 rpm, and some as high as 500,000 rpm. Even without the application of sideloads, these rotational velocities cause substantial amounts of friction to develop in the bearing assembly. In virtually all commercially available dental handpieces, friction is reduced by lubricating the bearing assembly either continuously, as by flowing a lubricant mist about the assembly, or by periodic lubrication, such as during cleaning and sterilization of the handpiece.

While lubrication of the bearing assemblies ameliorates somewhat the friction problems encountered, the need for lubrication creates other problems. For instance, it is difficult to insure the delivery of the precise amount of lubricant needed. Often, this is a result of different approaches to lubrication applied by users in the field. Lubricants also create problems in sterilization.

When high speed dental handpieces were first introduced in the 1960's, the life of the typical lubricated anti-friction bearing assembly was less than about 10 hours. Over the years, some progress has been made in the manufacture of small anti-friction bearings so that, today, a commercially satisfactory dental handpiece must be capable of surviving 2,000 hours of life cycle testing. A life cycle test involves five seconds of no rotation, acceleration to design speed and running (with a five second sideload applied at nine ounces) for a combined start-run-sideload time of 10 seconds, resulting in a total cycle time of 15 seconds. The same life cycle test procedure also applies to so-called low speed handpieces, i.e. those operating in a range of 5,000-60,000 rpm.

Thorough sterilization of handpieces generally involves the application of heat, such as in an autoclave or a chemiclave. In a typical autoclave, the handpiece, including its bearing assemblies, is subjected to a steam heat environment at a temperature of about 275° F. In a chemiclave, a vapor phase alcohol is used where some water and formaldehyde is also present. Typical sterilization time is about 15 to 20 minutes in both autoclave and chemiclave sterilization procedures. In a so-called dryclave procedure, temperatures may be as high as 375° F.

The high temperatures applied to handpieces during the aforementioned sterilization procedures exacerbate the corrosive effects of the moisture and chemicals on the bearing assemblies, and since many of the bearing assemblies incorporate retainers usually made of phenolic with organic fibers, for spacing the balls apart, the integrity of the retainers is also adversely affected by the heat and chemical reactions.

To place in perspective the life shortening effects of heat sterilization, it is estimated that a typical high speed dental handpiece which is not subjected to sterilization would last a dentist about 20 years with a minimum of repair (10-20% replacement of parts); whereas, the same handpiece, subject to heat sterilization as described heretofore, would last 1-2 years, requiring major repairs (80-90% replacement of parts).

BRIEF DESCRIPTION OF THE PRIOR ART

The following patents relate to dental handpieces. U.S. Pat. No. 3,071,861 to Saffir discloses a dental handpiece turbine assembly utilizing jewel bearings. See FIGS. 1 and 3. U.S. Pat. No. 4,568,642 to DeForrest discloses a jewel bearing for accepting thrust loads. See FIG. 4. U.S. Pat. No. 4,153,993 to Kataoka discloses a dental handpiece turbine bearing assembly utilizing air bearings and opposing magnets. U.S. Pat. No. 3,421,224 to Brehm discloses a dental handpiece turbine assembly fabricated of plastic materials. U.S. Pat. No. 3,248,792 to Staunt discloses a dental handpiece having a bearing ball retainer (FIGS. 19 and 20) fabricated of plastic material. U.S. Pat. No. 3,469,318, also issued to Saffir, is of general interest with respect to dental handpiece bearing assemblies, as is U.S. Pat. No. 4,249,896 issued to Kerfoot.

Anti-friction bearing assemblies fabricated of materials other than steel are disclosed in the following patents. U.S. Pat. No. 1,332,176 to Heindlhofer discloses an anti-friction bearing assembly having rolling elements fabricated of materials such as agate, quartz, topaz, garnets, emeralds, sapphires, and diamonds. U.S. Pat. No. 2,158,156 to Schroder discloses a bearing assembly fabricated completely of ceramic materials. U.S. Pat. No. 2,534,929 to Schultz discloses a ball bearing assembly which utilizes beryllium copper races in combination with glass balls and which can operate at low speeds under light load without lubrication. U.S. Pat. No. 3,097,897 to Taylor discloses an anti-friction bearing assembly composed of refractory materials, such as dense alumina, and raceways of dense titanium carbide cermet either with or without a spacer element to keep the balls separated in a raceway. U.S. Pat. No. 4,770,549 to Rokkaku and U.S. Pat. No. 4,792,244 to Yamashita disclose ceramic bearing assemblies of relatively recent vintage.

OBJECTS OF THE INVENTION

With the foregoing in mind, a primary object of the present invention is to provide a durable, non-lubricated, sterilizable handpiece.

Another object of the present invention is to provide a dental handpiece capable of withstanding the hostile environments encountered in heat sterilization procedures and of delivering a satisfactory service life with minimal maintenance.

As a further object, the present invention provides an improved dental handpiece which overcomes the limitations of known commercially available handpieces by being capable of operating without lubrication and of being sterilized repeatedly in high temperature hostile environments.

SUMMARY OF THE INVENTION

More specifically, the present invention overcomes the problems associated with known handpieces and achieves the foregoing objects by utilizing a bearing construction which does not require lubrication and which can withstand repeated exposure to high temperature sterilization procedures. In brief, this is accomplished by providing, in a powered hand held instrument having a proximal end portion adapted to mount a rotary tool for operating upon a portion of anatomy, a bearing assembly which includes an annular inner raceway, an annular outer raceway, and a plurality of rolling elements contained between the raceways and formed of a hard, dense, wear-resistant, inert material cooperable with the raceways to accommodate without lubrication high rotational speeds of the tool and repeated sterilization procedures without intervening lubrication.

BRIEF DESCRIPTION OF THE DRAWINGS

The foregoing and other objects, features and advantages of the present invention should become apparent from the following description, when taken in conjunction with the accompanying drawings which:

FIG. 2 is an enlarged cross-sectional view taken on line 2—2 of FIG. 1; and

DESCRIPTION OF THE PREFERRED EMBODIMENT

Figure 1:
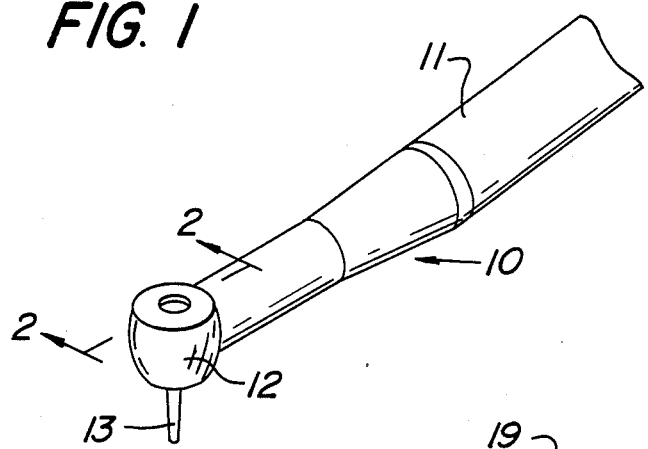
FIG. 1 is a fragmentary perspective view of a dental handpiece embodying the present invention.

Referring now to the drawings, FIG. 1 illustrates a dental handpiece 10 which embodies the present invention. Although the present invention has particular utility and will be described hereinafter with respect to a dental handpiece, it should be apparent that the present invention also has applicability to other handpieces, such as bone reamers, and other powered instruments used in a variety of medical applications wherein a rotary tool is used in close proximity with a portion of the anatomy, such as plaster cast rotary saws.

The illustrated handpiece 10 includes a handle portion 11 and a head 12 which rotatably mounts a tool, such as the burr 13 illustrated in FIG. 1. As best seen in FIG. 2, the head 12 is hollow and contains a turbine T having a plurality of peripheral buckets 14 mounted on a shaft 15. The burr 13 is releasably captured in a collet 16 connected to the shaft 15. The turbine T is rotated by air supplied by a conduit 17 extending lengthwise in the handle 11 and connected to a source of air under pressure, such as at a pressure of 30–35 psi.

The shaft 15 is rotatably mounted in the head 12 by means of upper and lower anti-friction bearing assemblies 18 and 19, respectively. The upper and lower anti-friction bearing assemblies 18 and 19 are of identical construction. Accordingly, reference hereinafter will be made to the lower anti-friction bearing assembly 19, it being understood that the same description applies to the upper bearing assembly 18.

As described thus far, the dental handpiece 10 is of conventional design and construction. A more detailed description of its structure, assembly and operation may be found in U.S. Pat. No. 4,249,896 issued to Kerfoot, the disclosure of pertinent portions of which is incorporated by reference herein.

As disclosed in the subject Kerfoot patent, the upper and lower anti-friction bearing assemblies 18 and 19 may be fabricated of stainless steel, such as the high-carbon chromium steel designated as SAE52100 stainless steel. Each bearing assembly, such as the lower bearing assembly 19, has an annular inner raceway 19a mounted to the shaft 15, an annular outer raceway 19b surrounding the inner raceway 19a, and a plurality of rolling elements 19c engaged between the inner and outer raceways 19a and 19b, respectively. The rolling elements 19c mount the inner raceway, and hence the shaft 15, collet 16, and burr 13 for rotation relative to the outer raceway 19b and its mounting head 12.

Preferably, as described in the Kerfoot patent, the rolling elements 19c are preloaded a predetermined amount in accordance with good design practice. In the embodiment of FIG. 2, the inner raceway of the upper anti-friction bearing assembly 18 is preloaded in the upward direction, and the inner raceway 19a of the lower bearing assembly 19 is preloaded in the axially downward direction. This preloading also preloads the rolling elements 19c in the lateral direction, i.e. transverse to the axis of rotation of the burr 13.

In the embodiment illustrated in FIG. 2, the rolling elements 19c are balls of a spherical shape. It should be apparent, however, that the present invention contemplates the use of rolling elements of other shapes and configurations, such as cylindrical, frusto-conical, and the like. As will be discussed, however, spherical elements formed of certain ceramic materials have been tested and found to provide a desirable service life.

In the aforedescribed Kerfoot patent, the rolling elements 19c are maintained in spaced relation between the inner and outer raceways by a retainer or spacer element, not shown. One of the purposes of the retainer is to prevent the rolling elements from contacting one another and, in so doing, generating friction and heat, thereby adversely affecting the performance and life of the bearing assembly. While the present invention eliminates the need for retainers, if used, the retainer or spacer may be fabricated of either a metallic or a non-metallic material, such as a phenolic resin, or of any of the modern ultra-high molecular weight engineering grade plastic materials commonly in use such as polyamides, polyimides and polycarbonates sold under the registered trademark TORLON.

As discussed heretofore, in the conventional dental handpiece, the bearing assemblies are lubricated either by a continuous supply of a lubricant which is contained within the air supplied to the turbine and circulated about the bearing assemblies, or by lubricating the bearing assemblies periodically, such as when the handpiece is taken out of service for general maintenance or for sterilization. Often, as recommended by some manufacturers, lubrication occurs after sterilization, but this is undesirable because the lubricant may contain contaminants that nullify the sterility of sterilization procedure.

Furthermore, as discussed heretofore, repeated sterilization of the handpiece reduces the useful life of the bearing assemblies by accelerating their degradation.

The present invention overcomes the aforementioned limitations of the conventional handpiece, and provides a handpiece which is durable, sterilizable and operates without lubrication. These advantages and others, are realized by fabricating at least the rolling elements of a non-metallic material, such as a ceramic material. With rolling elements of such material, the retainer may even be eliminated entirely.

The materials of which the rolling elements are fabricated should be hard, dense, wear-resistant, and inert, in addition to being non-metallic. A preferred material has a density of less than about 5.0 g/cm$^3$, a hardness of at least about 75 Rockwell C. at 20° C. and a coefficient of dry sliding friction of less than about 0.30 with respect to stainless steel of the type described above. The ceramic material is preferably sintered under heat and pressure into spheres of relatively small diameter, such as about 0.5 to 5.0 millimeters. When assembled into a bearing assembly, such as illustrated, no lubricants are supplied, the bearing assembly being essentially free of lubricants.

Other physical characteristics of a desirable rolling element material include the following, which are typical of silicon nitride used in the tested prototypes to be described:

| Characteristic | Value |
| --- | --- |
| Flexural Strength | 140 × 10$^3$ psi |
| Compressive Strength | 435 × 10$^3$ psi |
| Hertzian Compression Strength | 1450 × 10$^3$ psi (Constant stress max.) |
| Fracture toughness | 4.9 × 10$^3$ lbs. − cubic in.$^2$ |
| Youngs Modulus | 45 × 10$^6$ psi |
| Thermal Expansion | 1.9 × 10$^{-6}$ per deg. F. |
| Thermal Expansion | 220 BTU − in./hr.−ft$^2$ deg.−F. |
| Maximum Use Temp. | 2370 deg. F. |
| Critical Quench Temp. | 1110 deg. F. |
| Hardness | 78 Rockwell C at 20° C. |

There are essentially two types of ceramic materials that find utility in the present invention. These materials may be grouped into non-oxide ceramics and oxide ceramics. Of the non-oxide ceramics, preferred materials include nitrides, carbides and borides. The most preferable include: silicon nitride, and silicon carbide. Oxide type ceramics include the following: aluminum oxide, zirconium oxide, zirconia (with or without surface treatment), and zirconia-toughened alumina. More specifically, of these ceramics, preferred materials include the following: boron nitride, Sintered Si$_3$N$_4$(silicon nitride), Sintered AlSiC, boron carbide, silicon oxynitride, boron oxynitride, titanium boride, boron nitride-titanium boride.

In the illustrated embodiment, only the rolling elements are fabricated of ceramic material. The inner and outer raceways are both fabricated of a bearing grade steel, such as: 440C stainless steel, M-50 bearing steel or SAE52100 steel. While these bearing steels are preferable as metals, other corrosion-resistant metals may be used for the raceways. If desired, however, one or both of the raceways may be formed of a ceramic material, like the ceramic material of the rolling elements, or they may be formed of a ceramic material which is compatible with the ceramic material of the rolling element. Economic considerations and use of conventional equipment augur in favor of the use, at present, of stainless steel for the inner and outer raceways.

Figure 3:
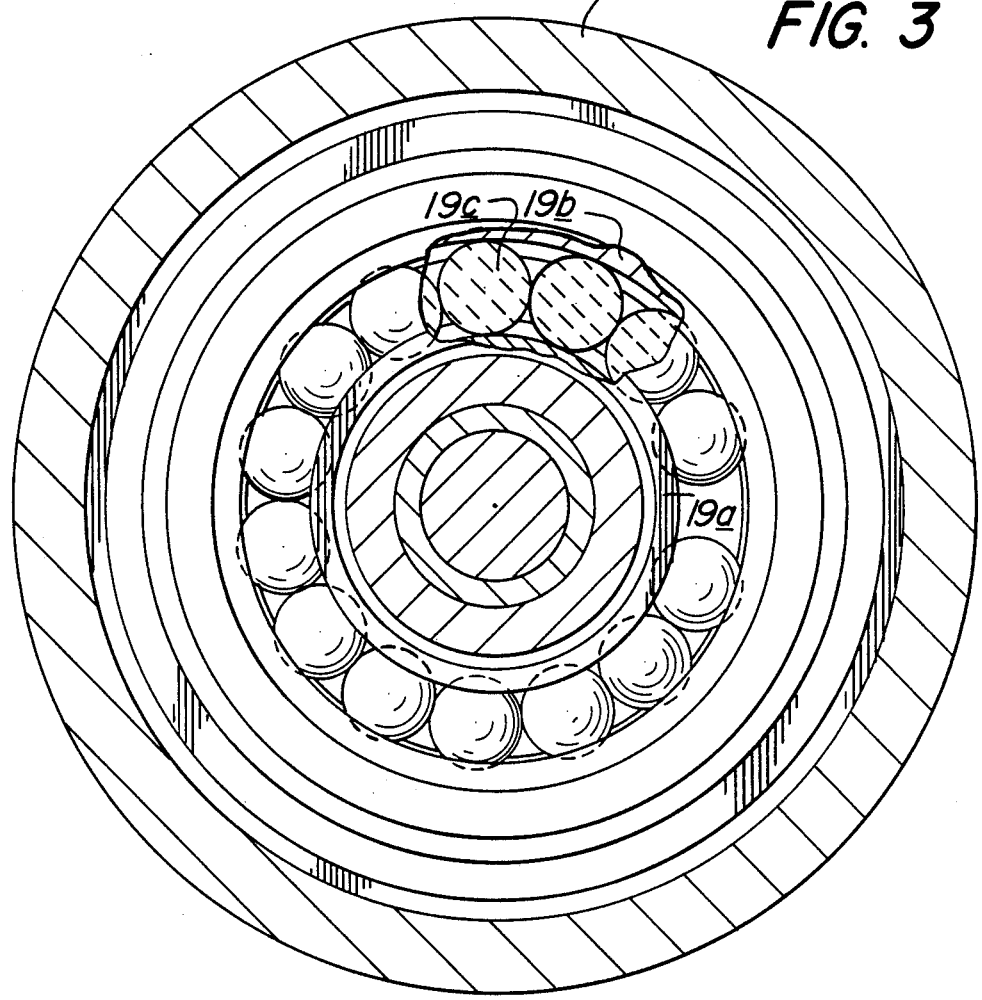
FIG. 3 is a further enlarged cross-sectional view taken on line 3—3 of FIG. 2.

In the absence of retainers, the rolling elements may group themselves in a manner illustrated in FIG. 3 as they rotate between the raceways. Thus, they may, and do, contact one another. However, the relatively low coefficient of friction between the rolling elements, (on the order of 0.17) renders unnecessary a retainer to maintain them in spaced apart relation as with conventional bearing assemblies. If desired, however, a retainer of either metallic or non-metallic plastic material such as discussed above may be used in those applications where retainers are indicated.

Silicon nitride has been formed into spheres one millimeter in diameter and assembled into bearing assemblies, without retainers, such as illustrated in FIG. 3. The bearing assemblies were installed in dental handpieces, such as illustrated in FIG. 1. The handpieces were subject to the operating cyclic life test procedure described heretofore. No lubrication was supplied to the bearing assemblies at any time.

The tests revealed that handpieces fabricated according to the present invention could operate satisfactorily over 2000 hours without failure and without lubrication. Satisfactory operation is defined as existing when the rotational speed of the tool remains within 10% of its design speed under no load conditions. Companion tests on handpieces of the same materials, but with heat sterilization occurring at 8 cycles/day intervals, established satisfactory performance for over 1000 hours, with tests continuing satisfactorily as of the date of execution of this application.

In view of the foregoing, it should be apparent that the present invention now provides an improved handpiece particularly suited for use in dental applications but also suitable for use in a variety of medical applications requiring sterilizable rotary tools. The handpiece of the present invention is resistant to the deleterious effects of corrosive heat sterilizing procedures. The handpiece eliminates entirely the need for either continuous or periodic lubrication since it operates free of lubricants. Furthermore, despite repeated sterilization and the absence of lubricants, the handpiece meets the requirements of commercial dependability and durability.

While a preferred embodiment of the present invention has been described in detail, various modifications, alterations and changes may be made without departing from the spirit and scope of the present invention and as defined in the appended claims.

I claim:

1. In a hand-held instrument particularly suited for use in medical and dental applications requiring periodic sterilization, the instrument including a handle, a rotary tool adapted to be carried by the handle, and an anti-friction bearing assembly for rotatably mounting the tool to the handle, the instrument handle adapted to being releasably secured to a power supply for the rotary tool to enable the instrument to be sterilized periodically, the bearing assembly including inner and outer raceways containing therebetween a plurality of rolling elements, the improvement wherein at least said rolling elements are formed of a hard, dense, wear-resistant non-metallic material, whereby the instrument can be sterilized repeatedly in hostile environments without adversely affecting the performance of the bearing assembly.

2. An instrument according to claim 1 wherein said bearing assembly is free of lubricants.

3. An instrument according to claim 1 wherein said rolling elements are randomly spaced apart between said raceways.

4. An instrument according to claim 1 wherein said rotary element material has a density of less than about 5.0 g/cm$^3$ and a hardness of at least about 75 Rockwell C at 20° C.

5. An instrument according to claim 1 wherein said material is a ceramic.

6. An instrument according to claim 1 wherein said material is silicon nitride.

7. An instrument according to claim 1 wherein said rolling elements include spheres.

8. An instrument according to claim 1 wherein said rolling elements have diameters in a range of about 0.5 to about 5.0 mm.

9. An instrument according to claim 1 wherein at least one of said raceways is of a material like the material of said rolling elements.

10. In a powered hand held instrument having a proximal end portion adapted to mount a rotary tool for use upon or in proximity with a portion of anatomy, including a bearing assembly carried in said end portion for rotatably mounting said tool; said bearing assembly including an annular inner raceway, an annular outer raceway, and a plurality of rolling elements contained between said raceways for mounting them for motion relative to one another; the improvement wherein at least said rolling elements are formed of a hard, dense, wear-resistant non-metallic material cooperable with said raceways to accommodate without lubrication rotational speeds of said tool in excess of 300,000 rpm and to accommodate repeated sterilization procedures of said instrument without intervening lubrication.

11. An instrument according to claim 10 wherein said non-metallic material is a ceramic.

12. An instrument according to claim 11 wherein said ceramic is selected from the group consisting of nitrides, carbides and borides.

13. An instrument according to claim 12 wherein said material has a density of at least 5.0 g/cm$^3$, a hardness of at least 75 Rockwell C at 20° C., and a coefficient of dry sliding friction of less than about 0.30 with respect to stainless steel.

14. An instrument according to claim 13 wherein said material is silicon nitride.

15. A non-lubricated, sterilizable, powered hand held instrument for operating a rotary tool upon or in close proximity with a portion of anatomy, including a bearing assembly carried in said instrument for rotatably mounting said tool to said instrument; said bearing assembly including an annular inner raceway, an annular outer raceway, and a plurality of rolling elements contained between said raceways, at least said rolling elements being formed of a hard, dense, wear-resistant non-metallic material cooperable with said raceways to accommodate, without lubrication, rotational speeds of said tool in excess of 300,000 rpm and to accommodate repeated sterilization procedures of said instrument without intervening lubrication.

16. An instrument according to claim 15 wherein at least one of said raceways is fabricated of a material like said material of said rolling elements.

17. An instrument according to claim 15 wherein said rolling elements are movable relative to one another in the space between said inner and outer raceways.

18. An instrument according to claim 15 wherein said rolling elements are fabricated of a ceramic material.

19. An instrument according to claim 18 wherein said ceramic material is selected from the group consisting of: silicon nitride, silicon carbide, aluminum oxide, and zirconium oxide.

20. An instrument according to claim 15 including a retainer for spacing the rolling elements apart between said raceways.

* * * * *

UNITED STATES PATENT AND TRADEMARK OFFICE
CERTIFICATE OF CORRECTION

PATENT NO. : 4,966,552
DATED : October 30, 1990
INVENTOR(S) : Donald I. Gonser

It is certified that error appears in the above-indentified patent and that said Letters Patent is hereby corrected as shown below:

In claim 13, column 8, line 5, replace "at least" with
-- less than about --.

Signed and Sealed this

Twenty-sixth Day of August, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,966,552 C1
DATED : October 14, 2003
INVENTOR(S) : Donald I. Gonser It is certified that error appears in the above-identified patent and that said Letters Patent is hereby corrected as shown below:

Column 1,
Line 50, "adaped" should read -- adapted --.

Signed and Sealed this

Twenty-fourth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 4,966,552 C1
DATED : October 14, 2003
INVENTOR(S) : Donald I. Gonser It is certified that error appears in the above-identified patent and that said Letters Patent is hereby corrected as shown below:

Column 7,
Line 36, "30,000 rpm" should read -- 300,000 rpm --.

Signed and Sealed this

Eighteenth Day of May, 2004

JON W. DUDAS
*Acting Director of the United States Patent and Trademark Office*

EX PARTE REEXAMINATION CERTIFICATE (4861st)
United States Patent
Gonser

(10) Number: US 4,966,552 C1
(45) Certificate Issued: Oct. 14, 2003

(54) STERILIZABLE NON-LUBRICATED ROTARY INSTRUMENT FOR DENTAL AND MEDICAL USE

(75) Inventor: Donald I. Gonser, Lancaster, PA (US)

(73) Assignee: Den-Tal-Ez, Inc., Philadelphia, PA (US)

Reexamination Request:
No. 90/004,803, Oct. 17, 1997
No. 90/004,926, Feb. 24, 1998

Reexamination Certificate for:
Patent No.: 4,966,552
Issued: Oct. 30, 1990
Appl. No.: 07/348,722
Filed: May 8, 1989

Certificate of Correction issued Aug. 26, 1997.

(51) Int. Cl.$^7$ .................................................. A61C 1/05
(52) U.S. Cl. ...................... 433/132; 415/229; 415/904; 384/492
(58) Field of Search .................... 433/132; 415/904, 415/170.1, 229; 384/492

(56) References Cited

U.S. PATENT DOCUMENTS

| | | | |
|---|---|---|---|
| 3,178,241 A | 4/1965 | Braunagel | 334/581 |
| 3,628,836 A | 12/1971 | Mulready et al. | 384/557 |
| 4,249,896 A | 2/1981 | Kerfoot, Jr. | 433/132 |
| 4,316,695 A * | 2/1982 | Knight, Sr. | 433/132 |
| 4,318,695 A * | 3/1982 | Lieb et al. | 433/132 |
| 4,629,707 A | 12/1986 | Wolfe | 501/97 |
| 4,634,300 A | 1/1987 | Takebayashi et al. | 384/548 |
| 4,650,592 A | 3/1987 | Dobbs et al. | 252/12.2 |

FOREIGN PATENT DOCUMENTS

| | | |
|---|---|---|
| EP | 0100380 | 2/1984 |
| EP | OPPO (1) | 3/1986 |
| EP | 0303758 | 2/1989 |
| EP | 0 423 313 | 6/1995 |
| FR | 2127291 | 10/1972 |
| FR | 2378204 | 8/1978 |
| JP | 63-229043 | 9/1988 |

OTHER PUBLICATIONS

Wedeven & Harris, Rolling Element, Machine Design, Aug. 8, 1987 pp. 72–76.
Hanson, Ceramics: Bearing Material of the Future, Inside Bearings, Apr. 1986, pp. 1–4.
Pitting Ceramic Bearings Against Steel, High Technology, Jul. 1986 (reprinted by Norton High Performance Ceramics, Northboro, MA).
Benz, D., *High Speed Bearings*, p. 325, *KEM Journal*, Apr., 1985, with English translation (3 pages).
Brauer, F.J., *Increasing Dental Speeds, US Armed Forces Medical Journal*, vol. VIII, No. 9, p. 1294, Sep., 1957.
Dvorak P., *Specialty Bearings Fill Nearly Every Niche, Machine Design*, vol. 60, No. 15, pp. 75–81, Jun. 1988.
Photocopy of brochure "European Design Engineering", *KEM*, Apr., 1985, front page and contents page, untranslated.
Photocopy of reprint of article in Aug. 17, 1987 *ADA News*, "Handpieces, High Speed", *Clinical Research Associates Newsletter*, Sep., 1988, vol. 12, Issue 9, 3 pages, unnumbered.
Photocopy of brochure "Midwest Handpiece Infection Control—Scrub and Dry; Lube and Operate; Bag and Cycle; Clean Fiber Optics; Lube and Operate Before Use", Midwest Sterilizable Handpieces, © 1989 Midwest Dental, Code No. 81836–0489, 2 pages, unnumbered.

(List continued on next page.)

*Primary Examiner*—John J. Wilson

(57) ABSTRACT

A handpiece particularly suited for medical/dental applications in which a rotary tool is used upon and in proximity with anatomical structures. The handpiece has an antifriction bearing assembly which mounts the rotary tool. At least the rolling elements of the bearing assembly are formed of ceramic material. The instrument may be sterilized repeatedly without requiring lubrication either in use or between sterilization cycles.

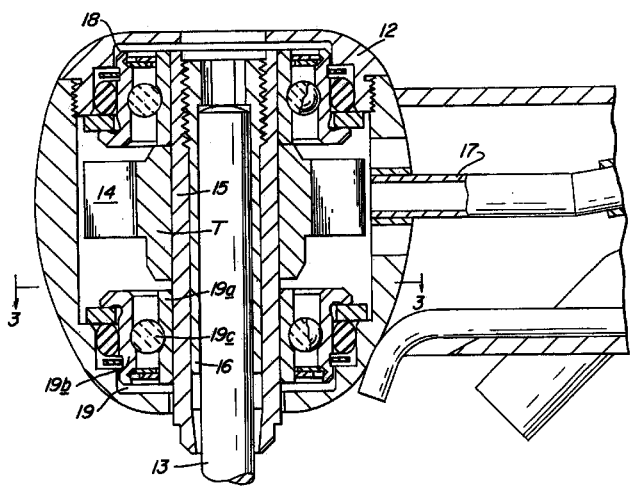

OTHER PUBLICATIONS

Photocopy of brochure "Midwest Handpiece Infection Control—Midwest Application of CDC/ADA Handpiece Infection Control Guidelines", 1 page, unnumbered, undated.

Photocopy of brochure "Midwest Handpiece Infection Control—Update No. 1—Turbonet/Sporicidin Handpiece Disinfection System", Feb. 2, 1988, 1 page, unnumbered.

Photocopy of brochure "Midwest Handpiece Infection Control—Update No. 2—Steri–Sleeve Cold Sterilizing Gauze Sleeve", Jul. 1, 1988, 1 page, unnumbered.

Photocopy of brochure "Midwest Handpiece Infection—Update No. 3—Decident Disposable Disinfectant Sleeve", Oct. 5, 1988, 1 page, unnumbered.

Photocopy of brochure "Midwest Handpiece Infection Control—Update No. 3A—Decident Disposable Disingectant Sleeve", Nov. 15, 1989, 1 page, unnumbered.

Photocopy of brochure "Midwest Handpiece Infection Control—Update No. 4—Vitawipes Disinfectant", Jan. 16, 1989, 1 page, unnumbered.

Photocopy of brochure "Midwest Handpiece Infection Control—Handpiece Autoclavability Information", © 1987 Sybron Corporation (HP–133–1187), cover sheet, Table of Contents, pp. 1–8, 2 pages (unnumbered page and back page).

Photocopy of brochure "Midwest—Quite–air.L™ Power Lever™ Exclusives, Operation and Maintenance Guide", © 1989 Midwest Dental, Form No. HP–192–0489, 4 pages (cover page and 3 unnumbered pages).

Photocopy of "Midwest Handpiece Infection Control—Handpiece Requirement Worksheet", Form No. HP–129–1087, 1 page, unnumbered, undated.

Photocopy of brochure "Midwest Handpiece Infection Control—Why Autoclave or Chemiclave Handpieces?", MIDWEST Sterilizable Handpieces, Form No. HP–128–0188, © 1988 Midwest Dental, 8 pages (cover page, 6 unnumbered pages, and back cover page).

Photocopy of brochure "Midwest Power Optic™ Handpiece Lighting System Installation Instructions", 7 pages (cover page and pp. 1–6), undated.

Photocopy of brochure "Midwest—There's a lot more to Midwest than meets the eye.", 4 pages (cover sheet and 3 unnumbered pages), Lit. #HP197, ©1989, Midwest Dental.

Photocopy of brochure "Midwest Power Lever™ Exclusives", 15 pages (cover sheet, and 14 unnumbered pages), Form No. HP–159–0688, ©1988 Midwest Dental.

Photocopy of brochure "Quite–air® Standard", 1 page, unnumbered, Code No. 81634–1187, ©1987 Sybron Corporation.

Photocopy of brochure "Midwest Handpiece Infection Control—Tradition•L with Power Lever High Speed Handpiece", Code No. 81611–0688, ©1988 Midwest Dental, 1 page, unnumbered.

Photocopy of brochure "Midwest Shorty® Air Motor", 10 pages (cover page, pp. 1–5, and 4 additional, unnumbered pages), Code No. 81762–0888, ©1988 Midwest Dental.

Photocopy of brochure "Midwest Shorty® Air Motor", 6 pages (cover page, pp. 1–10), undated.

Photocopy of brochure "KaVo guide for assistants", DMI DS–No. 2800/3–1,88e, 38 pages (cover page, contents page, and 36 unnumbered pages), undated.

Photocopy of brochure "KaVo INTRA matic A® System: Versatile and Effective", 5 pages (cover sheet and 4 additional, unnumbered pages), undated.

Photocopy of brochure "KaVo DMI Maintenance Instructions—Super–Torque LUX Turbine 630 BA . . . Super–Torque Turbine 630 CA . . .", DMI GA–No. 3335/2–V.88 USA, 22 pages (cover sheet, contents page, pp. 3–21, and back page), undated, KaVo Dentale Medizinischeinstrumente.

Photocopy of brochure "KaVo handpieces. May we offer you some assistance?", 25 pages (cover page, and 24 unnumbered pages), undated.

Photocopy of brochure "We're changing the way the world turns.", 989 10M ATC, 6 unnumbered pages, undated, Cerbec Ceramic Bearing Company.

Komeya, K., et al., "Development of Ceramic Antifriction Bearing*", ISAE Review, vol. 7, No. 3, Oct., 1986, pp. 72–79.

Mori, T., et al., "Properties of Silicon Nitride Rolling Bearing for High–Speed Air Turbine", Third International Symposium on Ceramic Materials and Components for Engines, Las Vegas, NV, Nov. 27–30, 1988, V.J. Tennery, Editor, cover page and pp. 1459–1468.

Photocopy of advertisement "KaVo DMI Quick Spray—The More Often You Spray, The Less Often You Pay.", undated, SCI–CAN, Division of Lux & Zwingenberger Ltd.

Ichikawa, Y., et al., "Research and Development—Static Load Capacity of Rolling Bearing with Ceramic Balls for Rolling Elements", Koyo® Engineering Report No. 136R, 7 pages (cover sheet, p. 5, and 5 unnumbered pages), undated, Kyo Seiko Co., Ltd.

Rokkaku, K., et al., "Performance and Application of Ceramic Bearings", Koyo Engineering Report for Application, pp. 1–10, undated.

Wedeven, L.D., et al., "ROLLING ELEMENT . . . New materials enable bearings to operate at higher temperatures and speeds, in crogenic regions, and in corrosive environments.", MACHINE DESIGN, Aug. 6, 1987, pp. 72–76.

Photocopy of brochure "High Performance Ceramics HPC", 7 unnumbered pages, undated, Norton Company.

Photocopy of brochure "Major Markets and Applications for Silicon Nitride Bearings", 2 pages, unnumbered, undated, Cerbec, Inc.

Photocopy of brochure "Produxte–Information 1–07d", 3 pages with translation ( 8.82, 30 and 31), undated, Saphirwerk Industrieprodukt (with translation).

Jahanmir, S., et al., "Friction and Wear of Silicon Nitride Lubricated by Humid Air, Water, Hexadecane and Hexadecane+0.5 Percent Stearic Acid©", American Society of Lubrication Engineers paper at the ASME/ASLE Tribiology Conference in Pittsburgh, PA, Oct. 20–22, 1988, pp. 1–10.

Kay, R., "The New Ball Bearings", BIKE TECH, pp. 1–4, Oct., 1988.

Photocopy of brochure "Technical Briefs—Dental Handpiece Beaarings", 2 pages (cover sheet and 1 unnumbered page), undated, Miniature Precision Bearings.

Hanson, R.A., "Ceramics: Bearing Material Of The Future", INSIDE BEARINGS, Apr. 1986, vol. 2, No. 1, pp. 1–4.

Photocopy of "Handpieces, Sterilization/Disinfection", Clinical Research Associates Newsletter, vol. 12, Issue 5, May 1988, 3 pages, unnumbered.

Photocopy of "High Speed Handpieces, Sterilizability Documentation", Clinical Research Associates, 4 pages, unnumbered, undated.

Photocopy of brochure "Hygienic Decontamination Procedures For Dental Handpieces—Contra–Angle Handpieces and Turbines", 12 pages (cover sheet, pp. 1–8, and 3 unnumbered pages), DMI DS–No. 2802/II.87e, undated, KaVo Dentale Medizinische Instrumente.

Photocopy of a portion of text entitled "bearing selection", M6 Catalog, Nov. 1979, pp. 52, 53.

Photocopy of Tom Rounds, Mar./Apr. 1960, pp. 10, 11.

Steinmann, D., "Herstellung, Eigenschften und Anwendung keramischer Werkstoffe auf der Basis von Siliziumnitrid", *Der Zuliefermarkt*, Mar. 1987, 4 pages, with attached English translation pp. 32–41.

Photocopy of GRW catalog, "Small, Miniature and Instrument Ball Bearings", 1988–1900?, 63 pages includes cover and contents pages, Gebrueder Reinfurt GmbH & Co. KG.

Photocopy of "MPB Precision Bearings and Bearing Products", Catalog 1–120–85, 88 pages (including cover sheet, pp. 1–84, back cover and 2 unnumbered pages), ©1985 MPB Corporation.

Photocopy of "Miniature Precision Bearings Division Capabilities:", Catalog 1–120–89, 88 pages (including cover sheet, pp. 1–84, back cover and 2 unnumbered pages), ©1989 MPB® Corporation.

Photocopy of "Working Data—Carpenter Stainless Steels", 185 pages (including cover sheet, Table of Contents, and pp. 1–182), undated, Carpenter Technology.

Benz, Dieter, "High–Speed Rolling Bearings", Apr. 1985, 9 pages (including pp. 16–20) (with translation).

"Precision for the Whole World", 9 pages (including pp. 24–27), 6/86, Saphirwerk Industrieproduke AG, (with translation).

"KaVo Bella–Torque 628", PR No. 7584/III 77 4 pages (including pp. 30–31), 1978, KaVo.

Product Information 1–07/d, 1982, 3 pages, Sapirwerk Industrie–produkte AG, (with translation).

"Common dimensions of precision balls made from: ruby, hard metal, ceramic and other superhard materials", 3 pages (including 30, 31), Jun. 1986, Saphirwerk Industrieproduke AG, (with translation).

Photocopy of brochure "Spheric", 6 pages (including pp. 1 and 2), Nov. 1987, Spheric Engineering Limited.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4–6 are cancelled.

Claims 1–3, 7–10, and 15 are determined to be patentable as amended.

Claims 11–14, and 16–20, dependent on an amended claim, are determined to be patentable.

1. In a hand-held *dental* instrument [particularly suited for use in medical and dental applications] requiring periodic sterilization, the *dental* instrument including a handle, a rotary tool adapted to be carried by the handle, and an anti-friction bearing assembly for rotatably mounting the tool to the handle, the *dental* instrument handle adapted to being releasably secured to a power supply for the rotary tool to enable the *dental* instrument to be sterilized periodically, the bearing assembly including inner and outer raceways containing therebetween a plurality of rolling elements, the improvement wherein at least said rolling elements are formed of [a hard, dense, wear-resistant non-metallic material,] *silicon nitride sintered under heat and pressure*, [whereby] *and* the *dental* instrument *maintains satisfactory operation after being* [can be] sterilized repeatedly in *a* hostile [environments without adversely affecting the performance of the bearing assembly] *environment*.

2. [An instrument according to claim 1 wherein said bearing assembly is free of lubricants] *In a hand-held instrument particularly suited for use in medical and dental applications requiring periodic sterilization, the instrument including a handle, a rotary tool adapted to be carried by the handle, and an anti-friction bearing assembly for rotatably mounting the tool to the handle, the instrument handle adaped to being releasably secured to a power supply for the rotary tool to enable the instrument to be sterilized periodically, the bearing assembly including inner and outer raceways containing therebetween a plurality of rolling elements, the improvement wherein at least said rolling elements are formed of silicon nitride sintered under heat and pressure, and the instrument maintains satisfactory operation after being sterilized repeatedly in a hostile environment and in the absence of intervening lubrication.*

3. [An instrument according to claim 1 wherein] *In a hand-held instrument particularly suited for use in medical and dental applications requiring periodic sterilization, the instrument including a handle, a rotary tool adapted to be carried by the handle, and an anti-friction bearing assembly for rotatably mounting the tool to the handle, the instrument handle adapted to being releasably secured to a power supply for the rotary tool to enable the instrument to be sterilized periodically, the bearing assembly including inner and outer raceways containing therebetween a plurality of rolling elements, the improvement wherein at least said rolling elements are formed of a hard, dense, wear-resisant non-metallic material,* said rolling elements are randomly spaced apart between said raceways, *and the instrument maintains satisfactory operation after being repeatedly sterilized in a hostile environment*.

7. [An] *A dental* instrument according to claim 1 wherein said rolling elements include spheres.

8. [An] *A dental* instrument according to claim 1 wherein said rolling elements have diameters in a range of about 0.5 to about 5.0 mm.

9. [An] *A dental* instrument according to claim 1 wherein at least one of said raceways is of a material like the material of said rolling elements.

10. In a powered hand held instrument having a proximal end portion adapted to mount a rotary tool for use upon or in proximity with a portion of anatomy, including a bearing assembly carried in said end portion for rotatably mounting said tool[;], said bearing assembly including an annular inner raceway, an annular outer raceway, and a plurality of rolling elements contained between said raceways for mounting them for motion relative to one another[;], the improvement wherein at least said rolling elements are formed of a hard, dense, wear-resistant non-metallic material cooperable with said raceways *and said bearing assembly maintains satisfactory operation* [to accommodate] without *intervening* lubrication *at* rotational speeds of said tool in excess of 30,000 rpm and [to accommodate repeated sterilization procedures of said instrument] *maintains satisfactory operation after being sterilized repeatedly in a hostile environment* without intervening lubrication.

15. [A] *In a* non-lubricated, sterilizable, powered hand held instrument *having a proximal end portion adapted to mount* [for operating] a rotary tool *for use* upon or in [close] proximity with a portion of anatomy, including a bearing assembly carried in said *end portion* [instrument] for rotatably mounting said tool to said instrument[;], said bearing assembly including an annular inner raceway, an annular outer raceway, and a plurality of rolling elements contained between said raceways, at least said rolling elements [being] *are* formed of a hard, dense, wear-resistant non-metallic material cooperable with said raceways, *said bearing assembly maintains satisfactory operation* [to accommodate,] without *intervening* lubrication[,] *at* rotational speeds of said tool in excess of 300,000 rpm and *maintains satisfactory operation after being sterilized repeatedly in a hostile environment* [to accommodate repeated sterilization procedures of said instrument] without intervening lubrication.

* * * * *